United States Patent [19]

Grudzinskas et al.

[11] 4,033,992

[45] July 5, 1977

[54] NOVEL COMPOUNDS OF THE 11-DEOXYPROSTAGLANDIN $E_3$, $F_{3\alpha}$, AND $F_{3\beta}$ SERIES

[76] Inventors: Charles Vincent Grudzinskas, 21 5th Ave., Nyack, N.Y. 10960; Martin Joseph Weiss, 975 Phillis Lane, Oradell, N.J. 07649

[22] Filed: Dec. 29, 1975

[21] Appl. No.: 645,066

Related U.S. Application Data

[60] Division of Ser. No. 526,772, Nov. 25, 1974, abandoned, which is a continuation-in-part of Ser. No. 300,011, Oct. 24, 1972, abandoned.

[52] U.S. Cl. .................. 260/456 R; 260/468 D; 260/488 R; 260/514 D; 424/305
[51] Int. Cl.$^2$ .................................. C07C 177/00
[58] Field of Search ............ 260/468 D, 514 D, C9

[56] References Cited

UNITED STATES PATENTS 3,773,795  11/1973  Basli et al. .................. 260/345.7

*Primary Examiner*—Robert Gerstl
*Attorney, Agent, or Firm*—Edward A. Conroy, Jr.

[57] ABSTRACT

This disclosure describes compounds of the 11-deoxyprostaglandin $E_2$, $F_{2\alpha}$, $F_{2\beta}$, $E_3$, $F_{3\alpha}$, and $F_{3\beta}$ series having bronchodilator activity.

14 Claims, No Drawings

NOVEL COMPOUNDS OF THE 11-DEOXYPROSTAGLANDIN E₃, F₃ₐ, AND F₃β SERIES

CROSS REFERENCE TO RELATED APPLICATION

This is a division of application Ser. No. 526,772, filed Nov. 25, 1974, which is a continuation-in-part of our copending application Ser. No. 300,011, filed Oct. 24, 1972. Both now abandoned.

BRIEF SUMMARY OF THE INVENTION

This invention relates to novel organic compounds of the prostaglandin class. More specifically, these compounds are members of the 11-deoxyprostaglandin $E_2$, $F_2\alpha$, $F_2\beta$, $E_3$, $F_3\alpha$, and $F_3\beta$ classes of the 15S and 15R configuration and may be represented by the following general formula:

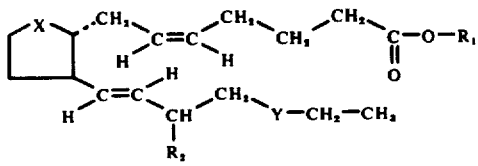

wherein $R_1$ is a member of the class consisting of hydrogen and alkyl radicals having from one to 12 carbon atoms; $R_2$ is a member of the class consisting of hydroxy, formyloxy, lower alkanoyloxy, and lower alkanesulfonyloxy radicals in the S or R configuration; X is a divalent radical chosen from the group consisting of

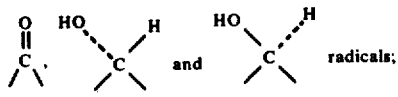

and Y is a divalent radical chosen from the group consisting of ethylene and cis-vinylene radicals, with the proviso that $R_2$ may not be hydroxy when X is keto and Y is ethylene. Suitable lower alkanoyloxy and lower alkanesulfonyloxy groups are those having up to four carbon atoms.

DETAILED DESCRIPTION OF THE INVENTION

The compounds of this invention belonging to the prostaglandin 2 series can be prepared from the methyl ester (I) of 15-O-acetylprostaglandin-A₂ which can be isolated from the gorgonid *Plexaura homomalla* (esper), a sea coral found in the Caribbean Sea. The isolation of the corresponding 15-epi (R) derivative from *Plexaura homomalla* is described by A. J. Weinheimer and R. L. Spraggins in *Tetrahedron Letters*, No. 59, 5185 (1969).

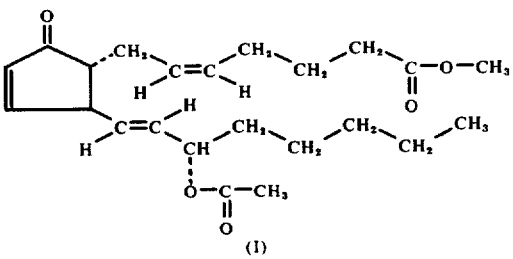

Treatment of diester (I) with sodium cyanoborohydride at a pH of about 3 results in the reduction of the 10,11-double bond and concommittant reduction of the ring carbonyl to the corresponding β- and α-alcohols (II + III). Oxidation of the intermediate 11-deoxyprostaglandin $F_2\beta$ /$F_2\alpha$ derivatives (II + III) then provides 11-deoxyprostaglandin E₂ diester (IV), saponification of which produces 11-deoxyprostaglandin E₂ (V). Mild treatment of (IV) with potassium carbonate results in preferential hydrolysis of the 15-O-acetate to give 11-deoxyprostaglandin E₂ methyl ester (VI). This sequence is outlined in the flowsheet which follows. A similar sequence starting with the 15-epi-(R)-PGA₂ diester corresponding to (I) produces the 11-deoxyprostaglandin E₂, $F_2\alpha$ and $F_2\beta$ derivatives in the 15-epi (15R) series.

FLOWSHEET A

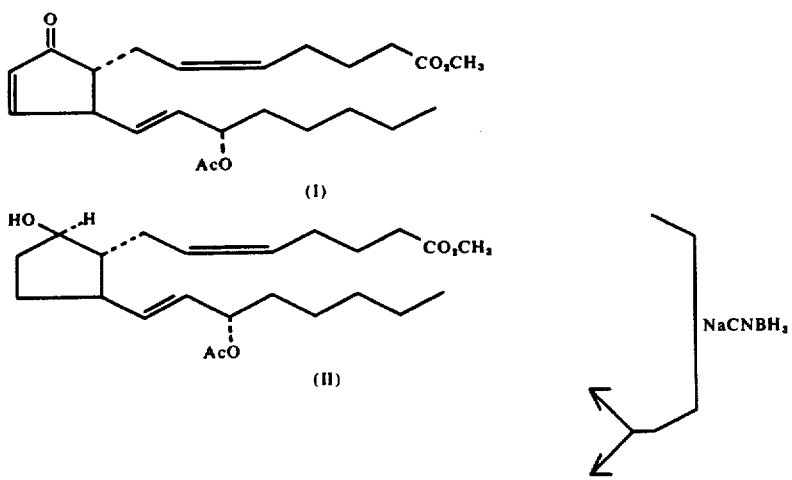

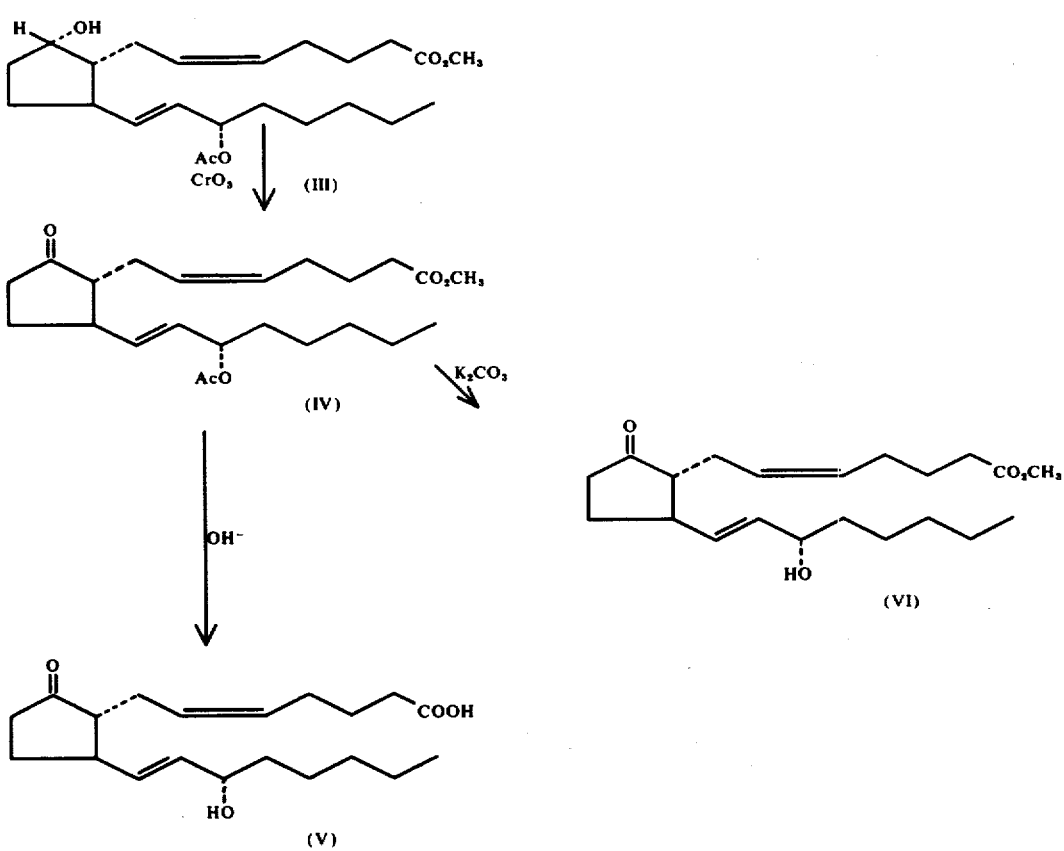

Treatment of 15-O-acetyl prostaglandin $A_3$ methyl ester (VII) with sodium cyanoborohydride by the above-described method produces the 15-O-acetate of 11-deoxyprostaglandin $F_2\beta$ /$F_2\alpha$ methyl ester (VIII + IX) which on chromic acid oxidation provides 11-deoxyprostaglandin $E_3$ 15-O-acetate methyl ester (X). Saponification then gives 11-deoxyprostaglandin $A_3$ (XI). These transformations are illustrated in the following flowsheet.

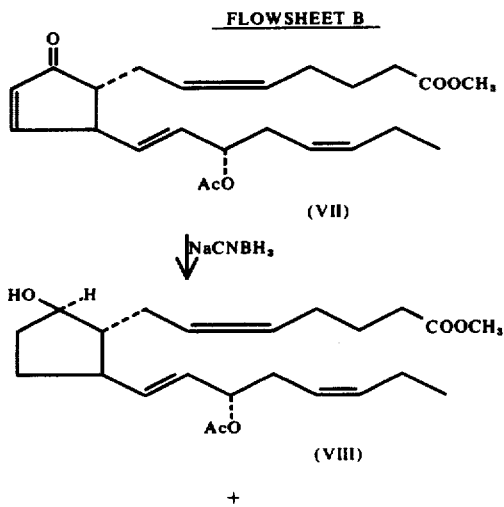

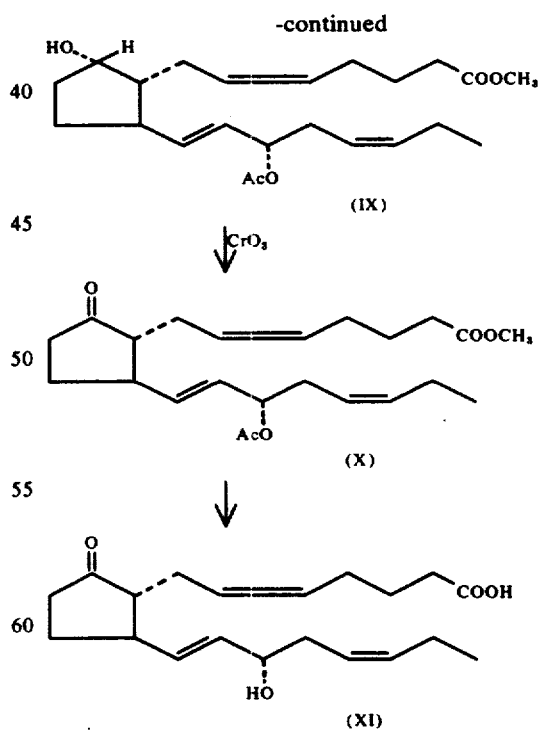

The process wherein prostaglandins of the A series are treated with sodium cyanoborohydride followed by reoxidation to provide the corresponding 11-deoxyprostaglandins is novel and useful and is to be considered a part of this invention.

Th products of this invention have the 15-oxy function in the S ("normal") configuration or the alternative R ("epi") configuration. Interconversion of compounds from the S to the R configuration and vice versa is possible and can be accomplished by two procedures, illustrated in the flowsheet below.

Treatment of 11-deoxyprostaglandin $E_2$ methyl ester (15-S configuration) with a solution of sodium formate in formic acid induces racemization of the 15-oxy function and a mixture of the 15(R) and 15(S) formyloxy derivatives (XIII) and (XII), respectively, are obtained. Separation of this mixture(after di-O-formylation) by chromatography provides the individual components: the origianal 15(S)-ol (XIV) and the inverted 15(R)-ol (XVII).

Epimerization of the 15(S)-ol (XIV) can be accomplised by conversion to a sulfonyloxy derivative (XV),

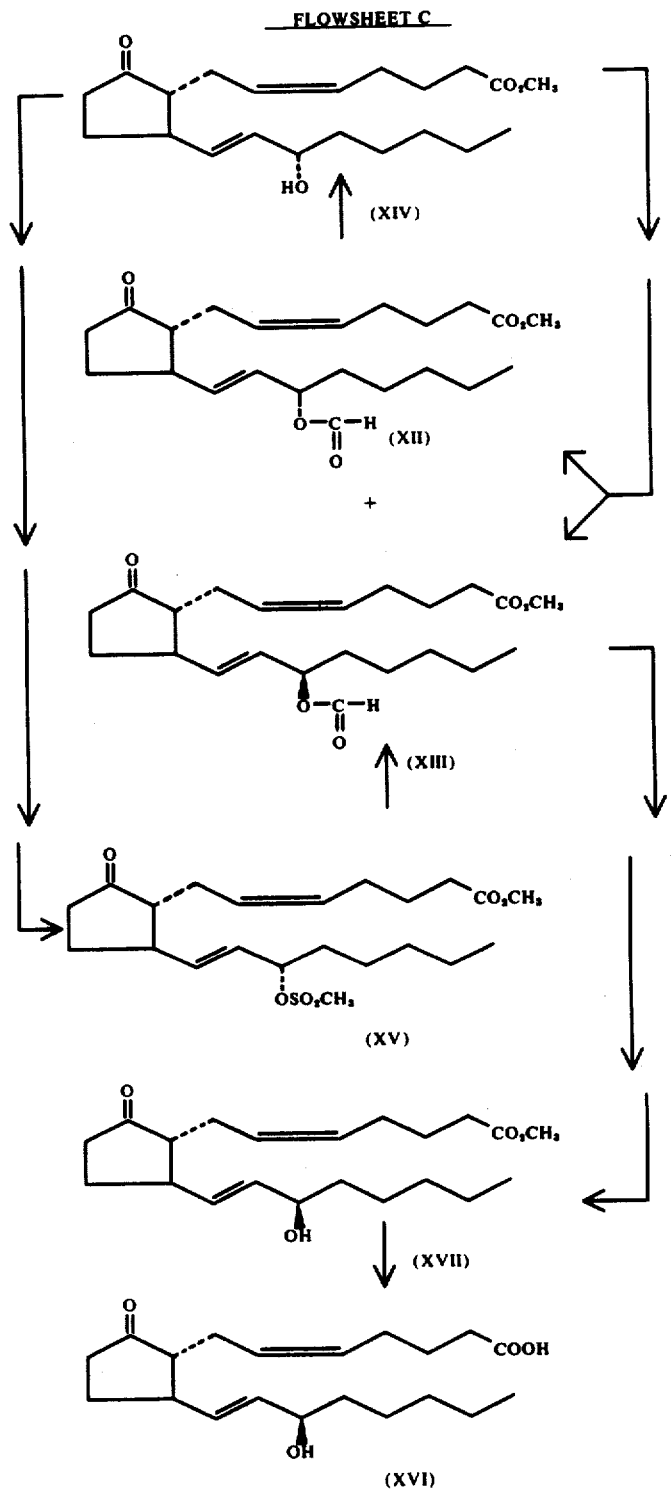

FLOWSHEET C such as methanesulfonyloxy, by treatment with methanesulfonic acid anhydride at low temperatures in the presence of an organic base such as triethylamine. The sulfonyloxy derivative (XV) is then treated with tetraethylammonium formate in a suitable organic solvent to produce the inverted 15(R)-formyloxy derivative (XIII). Formate hydrolysis then provides the 15(R)-alcohol (XVII).

These epimerization and racemization procedures can be applied in an entirely similar sequence in the reverse manner starting with the 15-epi (R) ester corresponding to (XIV).

Esterification of the free 15-hydroxy function as well as of the free carboxylic acid function by the usual procedures provides the other ester derivatives of this invention.

The 9-carbonyl function of the 11-deoxy derivatives of this invention can be reduced to an alcohol function. When this reduction is carried out with sodium borohydride a mixture of 9α- and 9β-hydroxy products is obtained. When the reduction is carried out with lithium perhydro-9β-borophenalylhydride (XVIII) [H. C. Brown and W. C. Dickason, *Journ. Amer. Chem. Soc.*, 92, 709 (1970)] the product is predominantly, if not completely, the 9α-hydroxy derivative.

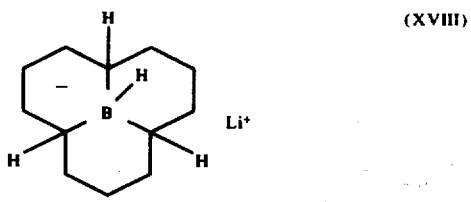

(XVIII)

The examples of this invention gives products in which the asymetric carbon atoms at position 8 and 12 (see formula I) are in the natural configuration and the products are thus members of the "l " series. This invention however embraces all optical isomers, enantiomorphs, diasteriomers and racemates corresponding to these "l " enantiomers.

The novel compounds of the present invention (and those wherein $R_2$ is hydroxy when X is keto and Y is ethylene) are effective inhibitors of gastric acid secretion and of ulcer development in experimental animals, and thus are potentially valuable as agents for the control of gastric acid secretion and of gastric erosion and as anti-ulcer agents. Gastric acid secretion inhibitory action was measured by the "Shay rat" procedure with some modifications as follows.

The rats (male, CFE strain) were starved for 48 hours (water was given ad libitum) to permit evacuation of stomach contents. On the morning of the experiment, under ether anesthesia, the abdominal region was shaved and a midline incision (1–1½inches) was made with a scapel. With the help of a closed curved hemostat the duodenum was picked up. Upon getting the duodenum into view, fingers were used to pull the stomach through the opening, the stomach was then greatly manipulated with fingers to rid the stomach of air and residual matter which were pushed through the pylorus. Two-5 inch sutures were drawn under the pyloric-duodenal juncture. A ligature, at the juncture, was formed with one of the threads. The second ligature was also formed but not tightened.

The test compound or the vehicle, usually 1 ml./100 g. body weight, were injected into the duodenum as close as possible to the first ligature. After injection the second ligature was tightened below the injection site to minimize leakage. The stomach was placed back through the opening into the abdominal cavity, the area of incision was washed with saline and the incision was closed with autoclips. (Occasionally, instead of an intraduodenal injection, animals were dosed by the oral or subcutaneous route. In the latter case, dosing as done 30 to 60 minutes before the operation.)

Three hours later, the rats were decapitated and exsanguinated, taking care that blood did not drain into the esophagus. The abdominal cavity was exposed by cutting with scissors and the esophagus close to the stomach was clamped off with a hemostat, the stomach was removed by cutting above the hemostat (the esophagus was cut) and between the two sutures. Extraneous tissue was removed, the stomach washed with saline and blotted on gauze. A slit was carefully made in the stomach which was held over a funnel and the contents were collected in a centrifuge tube. The stomach was further cut along the outside edge and turned inside out. Two ml. $H_2O$ were used to wash the stomach contents into the respective centrifuge tube. The combined stomach contents and wash were then centrifuged out for 10 minutes in the International Size 2 Centrifuge (setting at 30). The supernatant was collected, volume measured and recorded, 2 drops of a phenolphthalein indicator (1% in 95% ethanol) were added and the solution was titrated with 0.02N NaOH (or with 0.04N NaOH when large volumes of stomach contents were encountered) to pH 8.4 (because of usual coloring of the stomach contents, phenolphthalein was only used to permit visual indication that the end point was near) and the amount of acid present was calculated.

Compounds inducing inhibition of gastric acid secretion of 20% or more were considered active. In a representative operation, and merely by way of illustration, the results obtained with this assay with typical compounds of the present invention are given in Table I below.

TABLE I

| Compound | Intraduodenal dose, mg./kg. of body weight | Percent Inhibition |
|---|---|---|
| l-11-deoxyprostaglandin $E_1$ | 50 | 97 |
| l-11-deoxyprostaglandin $E_2$ | 12.5 | 42 |
| l-11-deoxyprostaglandin $F_{2\alpha}$ | 50 | 98 |

Another assay useful for determining potential anti-ulcer agents is carried out in the following manner.

Rats were starved for 48 hours (water was given as libitum). Indomethacin (20 mg./kg. of body weight) was administered by the subcutaneous route and one-half the dose of the test compound was administered by gavage at the same time. After 3 hours, the second half of the test compound was administered also by gavage. Five hours after the administration of Indomethacin the animals were decapitated and the stomachs removed. The stomachs were washed with distilled water, blotted on gauze, cut along the larger curvature, and the contents rinsed with distilled water. The stomachs were spread out, pinned on a cork and visualized under magnifying glass for ulcers. The critera for scoring of ulcers was as previously reported. [Abdel-Galil et al. *Brit. J. Pharmac. Chemotherapy* 33:1–14 (1968)].

Score

0 — Normal stomach
1 — Petechial hemmorrhage or pin point ulcers
2 — 1 or 2 small ulcers
3 — Many ulcers, a few large
4 — Many ulcers, mainly large Control animals treated with Indomethacin but not test compound consistently give scores of about 2.5–3.5. Control animals treated with neither Indomethacin nor test compound give scores of about 0.5–0.8. The results obtained in this assay with typical compounds of the present invention are set forth in the table below. Compounds diminishing the control ulcer score by 0.5 unit or more are considered to be active

TABLE II

| Compound | Total oral dose; mg./kg. of body weight | Score Treated Animals | Controls |
|---|---|---|---|
| l-11-deoxyprostaglandin $E_2$ | 12.5 | 1.2 | 2.7 |
| l-11-deoxyprostaglandin $F_{2\alpha}$ | 50 | 1.3 | 2.8 |

It is further to be noted that although prostaglandins in general are not considered to be effective when administered by the oral route, the compounds of this invention are effective orally.

This invention embraces the oral and parenteral use of the compounds of this invention for the treatment of gastric hypersecretion, gastric erosion, and peptic ulcers as well as for the prevention of peptic ulcers.

Bronchodilator activity was determined in guinea pigs against bronchospasms elicited by intravenous injections of 5-hydroxytryptamine, histamine, or acetylchlorine by the Konzett procedure. [See J. Lulling, P. Lievens, F. El Sayed and J. Prignot, *Arzneimittel-Forschung*, 18,995 (1968).] This activity is expressed as an $ED_{50}$ determined from the results obtained with three logarithmic cumulative intravenous doses.

Thus, l-11-deoxyprostaglandin $E_2$ when tested by this procedure produces the following activity.

| | $ED_{50}$, mcg./kg. Spasmogenic Agent | |
|---|---|---|
| 5-hydroxytryptamine | histamine | acetylcholine |
| 5.2 | 5.2 | 10 |

This invention embraces the oral, parenteral and aerosol use of the compounds of this invention (and those wherein $R_2$ is hydroxy when X is keto and Y is ethylene) as a brochodilator and for the treatment and prevention of brochial asthma.

The novel compounds of the present invention also have potential utility as hypotensive agents, antimicrobial agents, anticonvulsants, abortifacients, agents for the induction of labor, agents for the induction of menses, fertility-controlling agents, central nervous system regulatory agents, salt and water-retention regulatory agents, diuretics, fat metabolic regulatory agents, serum-cholesterol lowering agents, anti-inflammatory agents, and as inhibitors of platelet aggregation. Certain of the novel compounds of this invention possess utility as intermediates for the preparation of other of the novel compounds of this invention.

Also embraced within the scope of the present invention are the non-toxic pharmaceutically acceptable cationic salts of the prostanoic acid derivatives of the present invention when $R_1$ is hydrogen. The cations comprised in these salts include, for example, the non-toxic metal cations such as the sodium ion, potassium ion, calcium ion, and magnesium ion as well as the organic amine cations such as the tri(lower alkyl)amine cations (e.g., triethylamine), procaine, and the like.

The novel compounds of the present invention and their non-toxic pharmaceutically acceptable salts (when $R_1$ is hydrogen) have thus been found to be highly useful as bronchodilators and for inhibiting the formation of gastric ulcers in mammals when administered in amounts ranging from about 0.05 mg. to about 30 mg. per kg. of body weight per day. A preferred dosage regimen for optimum results would be from about 0.05 mg. to about 15 mg. per kg. of body weight per day, and such dosage units are employed that a total of from about 3.5 mg. to about 1.0 gm. of active ingredient for a subject of about 70 kg. body weight are administered in a 24 hour period. The compounds of the present invention may be administered by any convenient route such as orally, intraperitoneally, subcutaneously, intramuscularly or intraveneously.

Compositions according to the present invention having the desired clarity, stability and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol and polyethylene glycols. The polyethylene glycols consist of a mixture of non-volatile, normally liquid, polyethylene glycols which are soluble in both water and organic liquids and which have molecular weights of from about 200 to about 1500. Although the amount of active compound dissolved in the above vehicle may vary from 0.10% to 10.0% by weight, it is preferred that the amount of active compound employed be from about 3.0% to about 9.0% by weight. Although various mixtures of the aforementioned non-volatile polyethylene glycols may be employed, it is preferred to use a mixture having an average molecular weight of from about 200 to about 400.

In addition to the active compounds, the parenteral solutions may also contain various preservatives which may be used to prevent bacterial and fungal contamination. The preservatives which may be used for such purpose are, for example, myristyl-gamma-picolinium chloride, phenyl mercuric nitrate, benzalkonium chloride, phenethyl alcohol, p-chlorophenyl-α-glycerol ether, methyl and propyl parabens, and thimerosal. As a practical matter it is also convenient to employ antioxidants. Suitable antioxidants include, for example, sodium bisulfite, sodium metabisulfite, and sodium formaldehyde sulfoxylate. Generally, from about 0.05% to about 0.2% concentrations of antioxidant are employed.

For intramuscular injection, the preferred concentration of active compound is 0.25 to 0.50 mg./ml. of the finished compositions. They are equally adapted to intravenous administration when diluted with water or diluents employed in intravenous therapy such as isotonic glucose in appropriate quantities. For intravenous use, initial concentrations down to about 0.10 to 0.25 mg./ml. of active compound are satisfactory. They are also adapted to oral administration when diluted with drinking water.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the compounds may be incorporated with excipients and used in the form of tablets, troches, capsules, elixirs, suspensions, syrups, wafers, and the like. Such compositions and preparations should contain at least 0.1% of active compound. The percentage of the compositions and preparations may, of course, be varied and may conveniently be between about 5% to about 25% of the weight of the unit. The amount of active ingredient in such therapeutically useful compositions is such that a suitable dosage will be obtained. Preferred compositions or preparations according to the present invention are prepared so that an oral dosage unit form contains between about one and 200 milligrams of active compound.

The tablets, troches, pills, capsules and the like may also contain the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills or capsules may be coated with shellac, sugar or both. A syrup or elixir may contain the active compounds, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed.

This invention will be described in greater detail in conjunction with the following specific examples.

EXAMPLE 1

Isolation of the methyl ester of 15-O-acetylprostaglandin $A_2$ from Plexaura Homomalla (esper)

Specimens of *Plexaura Homomalla* (esper) are collected in Puerto Rican waters, air dried and stored under a nitrogen atmosphere at 0° C. The cortex is removed, ground and extracted with isomeric hexanes. The organic solvent is evaporated in vacuo to afford a prostaglandin containing residue. The residue is dissolved in nitromethane and extracted with isomeric hexanes. The nitromethane solution is evaporated to give a residue that is approximately 50% by weight of the residue prior to the nitromethane treatment. This process, in addition to the removal of unwanted materials, largely fatty esters, also has the benefit of selectively removing the sterols that have nearly the same rf index on silica gel as that of the methyl ester of 15-O-acetylprostaglandin $A_2$.

Purification of the residue via dry column chromatography using acid washed silica gel and 5% ethyl acetate as elutant yields the 15-O-acetyl-prostaglandin $A_2$ methyl ester and prostaglandin $A_2$ methyl ester. The combined yield of the two prostaglandins is 1–2%.

The configuration of the C-15 carbon is established by degradation with ozone followed by chromic acid oxidation to yield $\alpha$-acetoxyheptanoic acid. The configuration of the acetoxy grouping is established by comparison of the circular dichromism curves of $\alpha$-acetoxyheptanoic acid and D-$\alpha$-acetoxypropanoic acid prepared from the calcium salt of D-lactic acid (R-configuration). Compounds of like configuration will display curves of the same sign. D-$\alpha$-acetoxypropanoic acid displays a negative circular dichromism curve whereas the degradation product, $\alpha$-acetoxyheptanoic acid gives a positive circular dichromism curve.

EXAMPLE 2

Preparation of 11-deoxyprostaglandin $E_2$ from 15-O-acetyl prostaglandin $A_2$ methyl ester To a solution of 1.04 g. of 15-O-acetylprostaglandin $A_2$ methyl ester in 5 ml. of methanol is added a solution of 209 mg. of sodium cyanoborohydride in 2 ml. of methanol. The solution is adjusted to pH 3 with 2N methanolic hydrogen chloride and maintained at this pH by addition of methanolic hydrochloric acid as necessary. After 90 minutes the solution is evaporated in vacuo, 5 ml. of water is added. The solution is saturated with sodium chloride and extracted with ether. The ether extracts are dried with magnesium sulfate and evaporated in vacuo to yield 1.02 g. of an oil consisting mainly of 11-deoxy-15-O-acetyl-prostaglandin $F_2\alpha$ /$F_2\beta$ methyl esters.

To a solution of 900 mg. of the above mixture of 11-deoxy-15-O-acetyl-prostaglandin $F_2\alpha$ /$F_2\beta$ methyl esters in 30 ml. of acetone at 0° C. is added 0.8 ml of a standard chromic acid solution. The solution is stirred 10 minutes and poured into 70 ml. of ice and water. The aqueous solution is extracted with ether. The ether solution is dried with magnesium sulfate and evaporated in vacuo to afford 830 mg. of 11-deoxy-15-O-acetyl-prostaglandin $E_2$ methyl ester as an oil.

To a solution of 11-deoxy-15-O-acetylprostaglandin $E_2$ methyl ester in methanol is added four equivalents of 2.5N aqueous sodium hydroxide. The solution is stirred for 3 hours, poured into water, saturated with sodium chloride and acidified with 6N aqueous hydrochloric acid to pH 3.

The acidic solution is extracted with ether. The ethereal extracts are dried with magnesium sulfate and evaporated in vacuo to afford 11-deoxyprostaglandin $E_2$; $\lambda$max: 3400–2700 cm$^{-1}$ (carboxyl and hydroxyl), 1745–1710 cm$^{-1}$ (saturated ketone and carboxyl groups).

EXAMPLE 3

Preparation of 11-deoxyprostaglandin $E_2$ methyl ester

To a suspension of 300 mg. potassium carbonate in 30 ml. of methanol is added 11-deoxy-15-O-acetylprostaglandin $E_2$ methyl ester in 1 ml. of methanol. The solution is stirred for 48 hours and is then acidified with 6N aqueous hydrochloric acid. The solution is diuted with water and extracted with ether. The ether solution is washed with brine, dried with magnesium sulfate and evaporated in vacuo to yield 540 mg. of crude product. The product is purified by dry column chromatography using acid washed silica gel and eluting with 20% ethylacetate in benzene; $\lambda$max: 3400 cm$^{-1}$ (hydroxyl), 1735 cm$^{-1}$ (saturated ketone and ester).

EXAMPLE 4

Epimerization of 11-deoxyprostaglandin $E_2$ methyl ester

To a solution of 24 mg. of 11-deoxyprostaglandin $E_2$ methyl ester (Example 3) in 0.5 ml. of methylene chloride at −5° C. is added 15 ml. of triethylamine followed by 28 mg. of methanesulfonic acid anhydride in 0.5 ml. methylene chloride. The solution is stirred at −5° C. for 30 minutes and then all solvents are removed in vacuo.

The residual 15-methanesulfonyloxy-11-deoxyprostaglandin $E_2$ methyl ester is dissolved in 5 ml. of ether and the ether solution is added to a flask containing 245 mg. of tetraethylammonium formate. The ether is evaporated in vacuo at −5° C. and replaced by 2 ml. of dry acetone. The solution is maintained at 10° C. for 18 hours. The acetone is removed in vacuo and the residue is dissolved in 10ml. ether. The ether solution is washed with 5 ml. of 5% aqueous sodium bicarbonate solution and 5 ml. of brine. The ether solution is dried with magnesium sulfate and the ether evaporated in vacuo to yield 26.7 mg. of 11-deoxy-15R-O-formylprostaglandin $E_2$ methyl ester as an oil.

Treatment of a solution of the 11-deoxy-15R-O-formylprostaglandin $E_2$ methyl ester in 0.5 ml. of methanol with a crystal of p-toluenesulfonic acid overnight yields 15R-11-deoxyprostaglandin $E_2$ methyl ester as an oil that chromatographs slightly ahead of the starting 15S 11-deoxyprostaglandin $E_2$ methyl ester on silica gel. The residue also contains some of the starting 15S material.

EXAMPLE 5

Recemization of 15S-11-deoxyprostaglandin $E_2$ methyl ester

To 13 mg. of 15S-11-deoxyprostaglandin $E_2$ methyl ester (Example 3) is added a solution of 5 mg. potassium carbonate in 0.5 ml. of 97% formic acid. The solution is stirred under nitrogen for 60 minutes. Benzene is added and the solution is evaporated in vacuo.

The residue is placed on a 2 mm. silica gel plate and developed with 20% ethyl acetate in benzene. The area corresponding to rf = 0.45–0.65 is removed and the compound is eluted off of the silica-gel with 20% methanol in chloroform. The silica-gel is filtered and the organic solvents are evaporated in vacuo to yield 9 mg. of a mixture of 11-deoxy -15-O-formylprostaglandin $E_2$ methyl ester and the corresponding 15R epimer.

The mixture of 15-O-formyl compounds is dissolved in 1 ml. of methanol and one small crystal of p-toluenesulfonic acid is added. The solution is stirred overnight to afford approximately a 1:1 mixture of 15S-11-deoxyprostaglandin $E_2$ methyl ester and 15R-11-deoxyprostaglandin $E_2$ methyl ester.

Thin layer chromatography on silica-gel indicates the newly formed epimer (15R) is slightly less polar than the starting (15S) epimer.

EXAMPLE 6

Preparation of 11-deoxy-15-epi(R)-prostaglandin $E_2$

Saponification of 11-deoxy-15-epi(R)-prostaglandin $E_2$ methyl ester (Example 4) by the method of Example 2 provides the subject product.

EXAMPLE 7

Preparation of 11-deoxy-15-epi(R)-prostaglandin $E_2$ and Esters

Treatment of 15R-15-O-acetylprostaglandin $A_2$ methyl ester [A. J. Weinheimer and R. L. Spraggins, *Tetrahedron Letters*, No. 59, 5185 (1969)] with sodium cyanoborohydride in the manner of Example 2 is productive of 11-deoxy-15-R-15-O-acetylprostaglandin $F_2\alpha$ /$F_2\beta$ methyl esters.

Oxidation with chromic acid of this $F_2\alpha$ /$F_2\beta$ mixture in the manner of Example 2 is productive of 15-R-15-O-acetyl-11-deoxyprostaglandin $E_2$ methyl ester. Total saponification in the manner of Example 2 provides 15-R-11-deoxyprostaglandin $E_2$.

Partial saponification with potassium carbonate in the manner of Example 3 provides 15R-11-deoxyprostaglandin $E_2$ methyl ester.

EXAMPLE 8

Epimerization of 11-deoxy-15-epi(R)-prostaglandin $E_2$ methyl ester

Treatment of 11-deoxy-15-epi(R)-prostaglandin $E_2$ methyl ester (Example 7) with methanesulfonic anhydride in the manner of Example 4 is productive of 11-deoxy-15-epi(R)-methanesulfonyloxyprostaglandin $E_2$ methyl ester, which when treated with tetraethylammonium formate in the manner of Example 4 provides 11-deoxy-15-O-formylprostaglandin $E_2$ methyl ester. Seponification of this diester by the method of Example 2 gives 11-deoxyprostaglandin $E_2$.

EXAMPLE 9

Preparation of 11-deoxyprostaglandin $F_2\alpha$ and 11-deoxyprostaglandin $F_2\beta$ Saponification by the method described in Example 2 of 11-deoxy-15-O-acetylprostaglandin $F_2\alpha$ /$F_2\beta$ methyl esters (Example 2) and separation of the resulting hydroxy acids by chromatography provides 11-deoxyprostaglandin $F_2\alpha$ and 11-deoxyprostaglandin $F_2\beta$ .

EXAMPLE 10

Preparation of 11-deoxyprostaglandin $E_2$ and Esters

To a solution of 100 mg. (0.3 mmole) of prostaglandin $A_3$ (prepared from Prostaglandin $E_3$ [E. J. Corey et al, *J. Amer. Chem. Soc.*, 93, 1490 (1971)] by acid catalyzed dehydration in 0.5N hydrochloric acid in 30% aqueous tetrahydrofuran for 3 days) in methanol is added diazomethane until a yellow color persists. The solvent is removed and the prostaglandin $A_3$ methyl ester is dissolved in 50 ml. benzene, and a 1N solution of acetic anhydride-pyridine in benzene is added and the solution is stirred until TLC analysis indicates complete conversion of the $PGA_3$ methyl ester to 15-O-acetyl prostaglandin $A_3$ methyl ester. The solvent is removed in vacuo and the residue is chromatographed on 50 gm. of Silicar CC–4® silica gel using 8% ethyl acetate in benzene.

The 15-O-acetyl $PGA_3$ methyl ester is dissolved in 1 ml. of methanol and 20 mg. of sodium cyanoborohydride is added. The solution is maintained at pH 3 (Methyl Orange Indicator) by the dropwise addition of 2N methanolic hydrogen chloride. After the reduction has been completed, the solution is diluted with 10 ml. of water, saturated with sodium chloride, and extracted with ether.

The ether extracts are dried with magnesium sulfate, filtered and concentrated in vacuo to yield a mixture of 11-deoxy-15-O-acetyl $PGF_3\alpha$ and $F_3\beta$ methyl esters. This product is dissolved in 1 ml. of acetone at 0° C. and 0.1 ml. of a standard chromic acid solution is added. After stirring for 15 minutes the solution is poured into 5 ml. of ice/water and the solution is extracted with ether. The ether is dried with magnesium sulfate and concentrated in vacuo to give 11-deoxy-15-O-acetylprostaglandin $E_3$ methyl ester. This crude material is purified by partition chromatography to yield pure 11-deoxy-15-O-acetylprostaglandin $E_3$ methyl ester.

A portion of the 11-deoxy-15-O-acetyl $PGE_3$ methyl ester (20 mg.) is dissolved in 1 ml. of methanol, sodium carbonate is added and the solution is stirred 5 days. Then 10 ml. of ether and 10 ml. of cold water is added. The aqueous solution is separated and extracted with ether. The ether extracts are combined, dried with magnesium sulfate and evaporated to give 11-deoxyprostandin $E_3$ methyl ester.

To a solution of 20 mg. 11-deoxy-15-O-acetylprostaglandin $E_3$ methyl ester in 0.5 ml. of methanol is added 0.1 ml. 2.5 N aqueous sodium hydroxide. After 3 hours the solution is diluted with 5 ml. of water, acidified to pH 3 with 2N hydrochloric acid, saturated with sodium chloride and extracted with ether to give 11-deoxyprostaglandin $E_3$; $\lambda$ max: 3400–2700 cm$^{-1}$(COOH, OH), 1730 cm$^{-1}$(ketone), 1710 cm$^{-1}$(COOH), 975 cm$^{-1}$(c=C); pmr(CDCl$_3$) : 4.15 (m, 1H, H-15), 5.4–5.7 (m. 6H, $H_{5,6,13,14,18}$ and $_{19}$).

EXAMPLE 11

Preparation of 11-deoxyprostaglandin $F_3\alpha$ and 11-deoxyprostaglandin $F_3\beta$ Saponification of the methyl esters of 11-deoxyprostaglandin $F_2\alpha$ and $F_2\beta$ (Example 10) by the procedure of Example 2 and separation of the resulting hydroxy acids by chromatograhy is productive of 11-deoxyprostaglandin $F_3\alpha$ and 11-deoxyprostaglandin $F_3\beta$ .

EXAMPLE 12

Preparation of 11-deoxyprostaglandin $F_2\alpha$

To a solution of 700 mg. (2.1 mmol) of 11-deoxyprostaglandin $E_2$ (Example 2) in 4 ml. of tetrahydrofuran at −78° C. is added 7.4 ml. of a 0.62M (4.6 mmol) solution of lithium perhydro-9b-boraphenalyl hydride in tetrahydrofuran. After 60 minutes 4 ml. of water is added, the cooling bath is removed and the solution is stirred 30 minutes.

The solution is diluted with 20 ml. of water and extracted twice with 25 ml. of ether. The aqueous solution is acidified with 6N hydrochloric acid, saturated with sodium chloride and extracted twice with 25 ml. of ether. The ether extracts are combined, dried with magnesium sulfate and are evaporated in vacuo to give 700 mg. of 11-deoxyprostaglandin $F_2\alpha$ contaminated with a small amount of 11-deoxyprostaglandin $F_2\beta$ . 11-deoxy $PGF_2\alpha$ : $\lambda$max 3400–2700 cm$^{-1}$ (COOH, OH), 1700 cm$^{-1}$ (COOH), 975 cm$^{-1}$(c=c); pmr (CDCl$_3$): 4.15 (m, 2H, $H_{15}$ and $H_9\beta$), 5.48 (m, 4H, $H_{5,6,13}$ and $_{14}$).

EXAMPLE 13

Preparation of 11-deoxyprostaglandin $F_3\alpha$

Treatment of 11-deoxyprostaglandin $E_3$ (Example 10) with lithium perhydro-9b-boraphenalyl hydride by the procedure described in Example 12 is productive of the subject compound.

EXAMPLE 14

Preparation of 11-deoxy-15-epi(R)-prostaglandin $F_2\alpha$

Treatment of 11-deoxy-15-epi(R)-prostaglandin $E_2$ (Example 6) with lithium perhydro-9b-boraphenalyl hydride by the procedure described in Example 12 is productive of the subject compound.

EXAMPLES 15–28

Treatment of the 11-deoxyprostaglandin acids listed in the table below with the indicated diazoalkane in the following manner provides the product 11-deoxyprostaglandin esters of the following table.

An ethereal solution containing a molar excess of diazoalkane is added to a solution of 11-deoxyprostaglandin in ether (or acetone). After 2 to 4 hours the solution is carefully evaporated under reduced pressure and the residual prostaglandin ester is purified in the usual way by chromatography on silica gel.

TABLE III

| Ex. | Starting 11-deoxy-prostaglandin carboxylic acid | Diazo-alkane | Product 11-deoxyprostaglandin ester |
|---|---|---|---|
| 15 | 11-deoxyprostaglandin $E_2$ | diazo-heptane | 11-deoxyprostaglandin $E_2$ heptyl ester |
| 16 | 11-deoxyprostaglandin $E_2$ | diazo-decane | 11-deoxyprostaglandin $E_2$ decyl ester |
| 17 | 11-deoxyprostaglandin $E_2$ | diazo-pentane | 11-deoxyprostaglandin $E_2$ pentyl ester |
| 18 | 11-deoxyprostaglandin $E_3$ | diazo-heptane | 11-deoxyprostaglandin $E_3$ heptyl ester |
| 19 | 11-deoxyprostaglandin $E_3$ | diazo-decane | 11-deoxyprostaglandin $E_3$ decyl ester |
| 20 | 11-deoxyprostaglandin $E_3$ | diazo-pentane | 11-deoxyprostaglandin $E_3$ pentyl ester |
| 21 | 11-deoxyprostaglandin $F_{2\alpha}$ | diazo-heptane | 11-deoxyprostaglandin $F_{2\alpha}$ heptyl ester |
| 22 | 11-deoxyprostaglandin $F_{2\alpha}$ | diazo-decane | 11-deoxyprostaglandin $F_{2\alpha}$ decyl ester |
| 23 | 11-deoxyprostaglandin $F_{2\alpha}$ | diazo-pentane | 11-deoxyprostaglandin $F_{2\alpha}$ pentyl ester |
| 24 | 11-deoxyprostaglandin $F_{3\alpha}$ | diazo-heptane | 11-deoxyprostaglandin $F_{3\alpha}$ heptyl ester |
| 25 | 11-deoxyprostaglandin $F_{3\alpha}$ | diazo-decane | 11-deoxyprostaglandin $F_{3\alpha}$ decyl ester |
| 26 | 11-deoxyprostaglandin $F_{3\alpha}$ | diazo-pentane | 11-deoxyprostaglandin $F_{3\alpha}$ pentyl ester |
| 27 | 11-deoxy-15-epi(R)-prostaglandin $E_2$ | diazo-decane | 11-deoxy-15-epi(R)-prostaglandin $E_2$ decyl ester |
| 28 | 11-deoxy-15-epi(R)-prostaglandin $F_{2\alpha}$ | diazo-heptane | 11-deoxy-15-epi(R)-prostaglandin $F_{2\alpha}$ heptyl ester |

EXAMPLES 29–41

11-Deoxy-15-O-alkanoyl prostaglandins E and their corresponding esters.

Treatment of 11-deoxyprostaglandins of Table IV below with the indicated alkanoyl chloride by the following procedure yields the product 11-deoxy-15-O-alkanoyl prostaglandins of the table.

To a solution of the 11-deoxy prostaglandin ester and 1.1 equiv. of pyridine in benzene or other suitable organic solvents is added a solution of 1.1 equiv. of the respective alkanoyl halide in dry benzene. The solution is stirred until the reaction reaches completion. The solvents are removed in vacuo and replaced by 0.1N sodium bicarbonate in 10% aqueous tetrahydrofuran. The solution is stirred for 30 minutes and diluted with water. The aqueous solution is acidified and extracted with ether. The ethereal solution is extracted with dilute hydrochloric acid, 5% aqueous sodium carbonate, washed with brine, dried with magnesium sulfate, and concentrated in vacuo to furnish the respective 11-deoxy-15-O-alkanoyl prostaglandin ester which is purified by chromatography on silica gel. The corresponding 11-deoxy-15-O-alkanoyl prostaglandin acid is obtained by substituting the free acid for the starting prostaglandin ester and using 2.2 equiv. of both pyridine and alkanoyl chloride. In addition, the back extraction of the ethereal solution with aqueous sodium carbonate is omitted.

shell capsules of a suitable size at a fill weight of 95 milligrams per capsule.

EXAMPLE 49

| Preparation of tablet formation | |
|---|---|
| Ingredient | Milligrams per Tablet |
| 11-deoxyprostaglandin $E_2$ heptyl ester | 10 |
| Lactose | 200 |
| Corn starch (for mix) | 50 |
| Corn starch (for paste) | 50 |
| Magnesium stearate | 6 |

The active ingredient, lactose and corn starch (for mix) are blended together. The corn starch (for paste) is

TABLE IV

| Ex. | Starting 11-Deoxy-prostaglandin | Alkanoyl Chloride | 11-Deoxy-15-O-alkanoylprostaglandin |
|---|---|---|---|
| 29 | 11-deoxyprostaglandin $E_2$ | Pentanoyl chloride | 11-Deoxy-15-O-pentanoylprostaglandin $E_2$ |
| 30 | 11-deoxyprostaglandin $E_2$ | Octanoyl chloride | 11-Deoxy-15-O-octanoylprostaglandin $E_2$ |
| 31 | 11-deoxyprostaglandin $E_2$ | Decanoyl chloride | 11-Deoxy-15-O-decanoylprostaglandin $E_2$ |
| 32 | 11-deoxyprostaglandin $E_2$ heptyl ester | Propionyl chloride | 11-Deoxy-15-O-propionylprostaglandin $E_2$ heptyl ester |
| 33 | 11-deoxyprostaglandin $E_2$ pentyl ester | Octanoyl chloride | 11-Deoxy-15-O-octanoylprostaglandin $E_2$ pentyl ester |
| 34 | 11-deoxyprostaglandin $E_3$ | Octanoyl chloride | 11-Deoxy-15-O-octanoylprostaglandin $E_3$ |
| 35 | 11-deoxyprostaglandin $E_3$ | Pentanoyl chloride | 11-Deoxy-15-O-pentanoylprostaglandin $E_3$ |
| 36 | 11-deoxyprostaglandin $E_3$ | Decanoyl chloride | 11-Deoxy-15-O-decanoylprostaglandin $E_3$ |
| 37 | 11-deoxyprostaglandin $E_3$ | Trimethylacetyl chloride | 11-Deoxy-15-O-trimethylacetylprostaglandin $E_3$ |
| 38 | 11-deoxyprostaglandin $E_1$ | Trimethylacetyl chloride | 11-Deoxy-15-O-trimethylacetylprostaglandin $E_1$ |
| 39 | 11-deoxyprostaglandin $E_3$ decyl ester | Butyryl chloride | 11-Deoxy-15-O-butyrylprostaglandin $E_3$ decyl ester |
| 40 | 11-deoxyprostaglandin $E_3$ heptyl ester | Heptanoyl chloride | 11-Deoxy-15-O-heptanoylprostaglandin $E_3$ heptyl ester |
| 41 | 11-deoxyprostaglandin $E_3$ pentyl ester | Decanoyl chloride | 11-Deoxy-15-O-decanoylprostaglandin $E_3$ pentyl ester |
| 42 | 11-deoxyprostaglandin $F_{3\alpha}$ | Octanoyl chloride | 11-Deoxy-15-O-octanoylprostaglandin $F_{3\alpha}$ |
| 43 | 11-deoxyprostaglandin $F_{1\alpha}$ | Decanoyl chloride | 11-Deoxy-15-O-decanoylprostaglandin $F_{1\alpha}$ |
| 44 | 11-deoxyprostaglandin $E_2$ methyl ester | Octanoyl chloride | 11-Deoxy-15-O-octanoylprostaglandin $E_2$ methyl ester |
| 45 | 11-deoxyprostaglandin $E_3$ methyl ester | Pentanoyl chloride | 11-Deoxy-15-O-pentanoylprostaglandin $E_3$ methyl ester |
| 46 | 11-deoxyprostaglandin $F_{3\alpha}$ heptyl ester | Octanoyl chloride | 11-Deoxy-15-O-octanoylprostaglandin $F_{3\alpha}$ heptyl ester |
| 47 | 11-deoxyprostaglandin $F_{2\alpha}$ decyl ester | Heptanoyl chloride | 11-Deoxy-15-O-heptanoylprostanglandin $F_{2\alpha}$ decyl ester |

EXAMPLE 48

| Preparation of capsule formulation | |
|---|---|
| Ingredient | Milligrams per Capsule |
| 11-deoxyprostaglandin $E_2$ pentyl ester | 10 |
| Starch | 80 |
| Magnesium stearate | 5 |

The active ingredient, starch and magnesium stearate are blended together. The mixture is used to fill hard suspended in water at a ratio of 10 grams of corn starch per 80 milliliters of water and heated with stirring to form a paste. This paste is then used to granulate the mixed powders. The wet granules are passed through a No. 8 screen and dried at 120° F. The dry granules are passed through a No. 16 screen. The mixture is lubricated with magnesium stearate and compressed into tablets in a suitable tableting machine. Each tablet contains 10 milligrams of active ingredient.

EXAMPLE 50

| Preparation of oral syrup formulation | |
|---|---|
| Ingredient | Amount |
| 11-deoxy-15-O-butylrylprosta-glandin $E_3$ decyl ester | 500 mg. |
| Sorbitol solution (70% N.F.) | 40 ml. |
| Sodium benzoate | 150 mg. |
| Sucaryl | 90 mg. |
| Saccharin | 10 mg. |
| Red Dye (F.D. & C. No. 2) | 10 mg. |
| Cherry flavor | 50 mg. |
| Distilled water    qs | 100 ml. |

The sorbitol solution is added to 40 milliliters of distilled water and the active ingredient is suspended therein. The sucaryl, saccharin, sodium benzoate, flavor and dye are added and dissolved in the above solution. The volume is adjusted to 100 milliliters with distilled water.

Other ingredients may replace those listed in the above formulation. For example, a suspending agent such as bentonite magma, tragacanth, carboxymethylcellulose, or methylcellulose may be used. Phosphates, citrates or tartrates may be added as buffers. Preservatives may include the parabens, sorbic acid and the like and other flavors and dyes may be used in place of those listed above.

EXAMPLE 51

| Preparation of intramuscular formulation | |
|---|---|
| Ingredient | Amount |
| 11-deoxyprostaglandin $F_{1\alpha}$ sodium salt | 0.25% |
| Parabens (4:1 mixture of methyl and propyl) | 0.1% |
| Water for injection    qs | 100% |

The parabens are dissolved in about one-half the volume of water for injection at 80° C. with stirring. The solution is cooled to below 40° C. and the active ingredient is dissolved therein.. The cooled solution is adjusted to final volume with water for injection and is then sterilized by sterile filtration through a suitable filter.

We claim:

1. A compound selected from the group embracing the 15(S) and 15(R) configurations and consisting of those of the formula:

$$\begin{array}{c} X \diagdown \diagup CH_2-CH\overset{cis}{=}CH-(CH_2)_3-\overset{O}{\overset{\|}{C}}-O-R_1 \\ \diagdown \diagup \\ CH\overset{trans}{=}CH-CH-CH_2-CH\overset{cis}{=}CH-CH_2-CH_3 \\ | \\ R_2 \end{array}$$

wherein $R_1$ is selected from the group consisting of hydrogen and alkyl having up to 12 carbon atoms; $R_2$ is selected from the group consisting of hydroxy, formyloxy, alkanoyloxy having up to four carbon atoms and alkanesulfonyloxy having up to four carbon atoms; X is a divalent radical selected from the group consisting of those of the formulae:

$$\overset{O}{\overset{\|}{C}}\diagdown , \quad \overset{HO}{\diagdown}\overset{H}{\diagup}\overset{}{C}\diagdown \quad \text{and} \quad \overset{HO}{\diagdown}\overset{H}{\diagup}\overset{}{C}\diagdown ;$$

and the pharmacologically acceptable cationic salts thereof when $R_1$ is hydrogen.

2. The compound according to claim 1 in the 15(S) configuration wherein $R_1$ is hydrogen, $R_2$ is hydroxy, and X is $$\overset{O}{\overset{\|}{C}}\diagdown ;$$

1—11-deoxyprostaglandin $E_3$.

3. The compound according to claim 1 in the 15(R) configuration wherein $R_1$ is hydrogen, $R_2$ is hydroxy, and X is $$\overset{O}{\overset{\|}{C}}\diagdown ;$$

1—11-deoxy-15-epi-prostaglandin $E_3$.

4. The compound according to claim 1 in the 15(R) configuration wherein $R_1$ is methyl, $R_2$ is hydroxy, and X is $$\overset{O}{\overset{\|}{C}}\diagdown ;$$

1-11-deoxy-15-epi-prostaglandin $E_3$, methyl ester.

5. The compound according to claim 1 in the 15(S) configuration wherein $R_1$ is n-heptyl, $R_2$ is hydroxy, and X is $$\overset{O}{\overset{\|}{C}}\diagdown ;$$

1-11-deoxy-15-prostaglandin $E_3$, n-heptyl ester.

6. The compound according to claim 1 in the 15(S) configuration wherein $R_1$ is hydrogen, $R_2$ is acetyloxy, and X is $$\overset{O}{\overset{\|}{C}}\diagdown ;$$

1-11-deoxy-15-O-acetylprostaglandin $E_3$.

7. The compound according to claim 1 in the 15(R) configuration wherein $R_1$ is hydrogen, $R_2$ is methanesulfonyloxy, and X is $$\overset{O}{\overset{\|}{C}}\diagdown ;$$

1-11-deoxy-15-O-epi-methane-sulfonylprostaglandin $E_3$.

8. The compound according to claim 1 in the 15(S) configuration wherein $R_1$ is hydrogen, $R_2$ is hydroxy, and X is

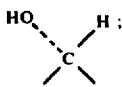

1-11-deoxyprostaglandin $F_3\alpha$.

9. The compound according to claim 1 in the 15(S) configuration wherein $R_1$ is methyl, $R_2$ is acetyloxy, and X is

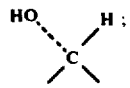

1-11-deoxy-15-O-acetylprostaglandin $F_3\alpha$ methyl ester.

10. The compound according to claim 1 in the 15(S) configuration wherein $R_1$ is methyl, $R_2$ is acetyloxy, and X is

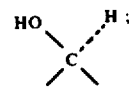

1-11-deoxy-15-O-acetylprostaglandin $F_3\alpha$ methyl ester.

11. The compound according to claim 1 in the 15(S) configuration wherein $R_1$ is n-decyl, $R_2$ is hydroxy, and X is

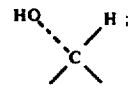

1-11-deoxyprostaglandin $F_3\alpha$ n-decyl ester.

12. The compound according to claim 1 in the 15(S) configuration wherein $R_1$ is hydrogen, $R_2$ is hydroxy, and X is

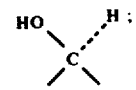

1-11-deoxyprostaglandin $F_3\alpha$.

13. The compound according to claim 1 in the 15(R) configuration wherein $R_1$ is hydrogen, $R_2$ is hydroxy, and X is

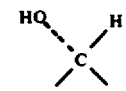

1-11-deoxy-15-epi-prostaglandin $R_3\alpha$.

14. The compound according to claim 1 in the 15(S) configuration wherein $R_1$ is n-heptyl, $R_2$ is hydroxy, X is

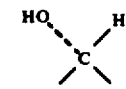

1-11-deoxyprostaglandin $F_3\alpha$ n-heptyl ester.

* * * * *